(12) United States Patent
Li et al.

(10) Patent No.: US 9,719,953 B2
(45) Date of Patent: Aug. 1, 2017

(54) SYSTEM AND PROCESS FOR DETERMINING AND ANALYSING SURFACE PROPERTY PARAMETERS OF SUBSTANCE BASED ON KINETIC METHOD

(75) Inventors: Rui Li, Chongqing (CN); Hang Li, Chongqing (CN); Xinmin Liu, Chongqing (CN); Zhenlun Li, Chongqing (CN); Jie Hou, Chongqing (CN); Hualing Zhu, Chongqing (CN); Laosheng Wu, Chongqing (CN)

(73) Assignee: SOUTHWEST UNIVERSITY, Bei Bei District, Chongqing (CN)

( * ) Notice: Subject to any disclaimer, the term of this patent is extended or adjusted under 35 U.S.C. 154(b) by 649 days.

(21) Appl. No.: 14/359,502

(22) PCT Filed: Jan. 20, 2012

(86) PCT No.: PCT/CN2012/070635
§ 371 (c)(1),
(2), (4) Date: Nov. 24, 2014

(87) PCT Pub. No.: WO2013/075403
PCT Pub. Date: May 30, 2013

(65) Prior Publication Data
US 2015/0076006 A1 Mar. 19, 2015

(30) Foreign Application Priority Data

Nov. 24, 2011 (CN) .......................... 2011 1 0378966
Nov. 24, 2011 (CN) .......................... 2011 1 0378979

(51) Int. Cl.
*G01N 27/26* (2006.01)
*G01R 29/24* (2006.01)

(52) U.S. Cl.
CPC ............. *G01N 27/26* (2013.01); *G01R 29/24* (2013.01)

(58) Field of Classification Search
CPC .............................. G01N 27/00; G01N 27/26
See application file for complete search history.

(56) References Cited

U.S. PATENT DOCUMENTS

| 7,394,279 B2 | 7/2008 | Lee et al. |
| 8,435,179 B2 * | 5/2013 | Goode, Jr. ........... A61B 5/0031 600/345 |

(Continued)

FOREIGN PATENT DOCUMENTS

| CN | 101393238 A | 3/2009 |
| CN | 101393239 A | 9/2012 |

OTHER PUBLICATIONS

International Search Report for corresponding International Patent Application No. PCT/CN2012/070635 mailed Sep. 6, 2012.

*Primary Examiner* — Susan D Leong
(74) *Attorney, Agent, or Firm* — Merchant & Gould P.C.

(57) ABSTRACT

A system and process for determining and analyzing surface property parameters of a substance based on kinetic method is provided. The system comprises a sample processing system and a detection system. The sample processing system includes a reactor (3), a collector for liquid to be tested (5), and a container for liquid to be tested (6). The detection system includes a detecting electrode (13), a concentration and activity operator, a kinetic data processor, a surface property operation module, and a result output module. The process comprises: having the substance to be tested to be treated with an electrolyte solution, measuring activity of liquid to be tested upon reaction at a pre-set time interval, and processing with the kinetic data processor and the surface property operation module, so as to obtain surface property parameters of the substance to be tested. The present invention adopts kinetic method of ion exchange to overcome the issues associated with long reaction equilibrium time, not easy to determine equilibrium and (Continued)

not easy to accurately determine the value of m. Five parameters of the substance surface property can be calculated with only intercept and gradient of the linear regression equation obtained from the kinetic data, and the total amount of surface charge can also be directly determined.

15 Claims, 2 Drawing Sheets

(56) References Cited

U.S. PATENT DOCUMENTS

| | | | | |
|---|---|---|---|---|
| 2008/0056946 | A1* | 3/2008 | Ahmad | A61B 5/097 422/68.1 |
| 2013/0071837 | A1* | 3/2013 | Winters-Hilt | C12Q 1/6869 435/6.11 |

* cited by examiner

SYSTEM AND PROCESS FOR DETERMINING AND ANALYSING SURFACE PROPERTY PARAMETERS OF SUBSTANCE BASED ON KINETIC METHOD

This application is a National Stage Application of PCT/CN2012/070635, filed 20 Jan. 2012, which claims benefit of Serial No. 201110378979.2, filed 24 Nov. 2011 in China and Serial No. 201110378966.5, filed 24 Nov. 2011 and which applications are incorporated herein by reference. To the extent appropriate, a claim of priority is made to each of the above disclosed applications.

TECHNICAL FIELD

The present invention relates to fields of colloid chemistry, interface chemistry, chemistry and chemical engineering, environmental protection, and material science and technology, and specially relates to a system and process for determining and analyzing surface property parameters of a substance based on kinetic method.

BACKGROUND

The surface properties of a substance, such as surface potential, total amount of electric charge on the surface, surface charge density, electric field intensity on the surface and specific surface area, etc., not only are widely used in science researches in the fields of colloid and interface chemistry, material science, life science, soil science, ecological and environmental science and the like, but also are widely used in chemical engineering fields such as papermaking, cement, ceramics, chemical mechanical polishing, coal slurry, coating, cosmetics, food industry, mixing and dispersion system. Thus, determination on the surface property parameters of a substance appears particularly important.

Currently, for determining the total amount of electric charge on the surface, ion adsorption indicator and potentiometric titration method are commonly used. When using ion adsorption, one first needs to know the amount contributed to electrostatic adsorption from the total adsorption amount at $H^+$ or $OH^-$. However, the adsorption amount of involved in electrostatic adsorption cannot be predicted, due to $H^+$ and $OH^-$ also involve adsorption of chemical bond. Thus, this method cannot determine the total amount of surface electric charge of a system containing variable charge under any pH value, any electrolyte concentration and any temperature. Further, the potentiometric titration method not only is not suitable for determining the total charge amount of a system containing permanent charge, but also is always questioned on its reliability, even for a variable charge system. Thus, so far there is no common method suited for determining total amount of substance surface charge in different conditions and different systems.

Currently, one method for determining a surface charge density of a substance is based on the following formula:

$$\sigma_0 = \frac{T_C}{S},$$

Wherein, $\sigma_0$ is surface charge density, $T_c$ is total amount of surface charge, and S is specific surface area.

Since the parameter of total amount of surface charge is required, the problem with determination of total amount of surface charge must also exist in the determination of surface charge density. Further, in the above formula, the specific surface area is also required. However, the result of the specific surface area may greatly vary, if different methods may be used to determine the specific surface area. Thus, for a method that determines surface charge density based on the parameter of specific surface area, the reliability of its result is hard to expect.

Conventionally, a second method for determining surface charge density is: upon obtaining the surface potential of the substance, correlation formula of Gouy-Chapman is used to indirectly obtain the surface charge density. However, up until now no widely applied method is available to accurately determine the surface potential. Thus, there are still difficulties to apply such method to determine surface charge density.

Currently, electric field intensity can be determined based on the below formula:

$$E_0 = \frac{4\pi}{\varepsilon}\sigma_0,$$

Wherein, $E_0$ is the surface electric field intensity, $\varepsilon$ is the media dielectric constant, e.g., water has $\varepsilon = 8.9 \times 10^{-10}$ $C^2/Jdm$. Due to depending on the surface charge density, same problem in determining surface charge density exists in determining surface electric field intensity.

In the prior art, there are a number of method for determining a substance specific surface area, such as commonly used inert gas adsorption method, ion negative adsorption method, glycol ethylene ether adsorption method, or glycerin adsorption method, etc. However, the results vary substantially by using these different methods for same substance.

In the present invention, substance surface potential is defined as the potential on the original surface of diffusion layer or OHP (outer Helmholtz surface) in the double electric layer. In the prior art, the method for determining substance surface potential includes: charge density method, negative adsorption method, positive adsorption method, dual-stage resonance (generation) method, pH indicator molecule method, fluorescence method, atomic force microscope method and Zeta potential method, and the like. All these methods have their own limitations. The charge density method, negative adsorption method, positive adsorption method and dual-stage resonance method are only suitable for determining surface potential of a constant charge sample of a single electrolyte system under neutral condition. The pH indicator molecule method, fluorescence method and atomic force microscope method may damage the condition of the substance surface per se, and thus the reliability of the result is difficult to say. Zeta potential method does not measure the surface potential. Rather, it measures the potential on the shear plane (or sliding surface) during electrophoresis, and the shear plane is often remote from the defined surface. The Zeta potential can be measured under different pH, electrolytes and temperature conditions. Since there is no method that can be widely used and accurately determine the surface potential under various conditions, Zeta potential has to be used as a substitute for surface potential. However, numerous studies over the years have shown that using Zeta potential to determine surface potential often is qualitative. In addition, Zeta potential method demands a very severe condition on the object to be tested, i.e., it requires that the particulate density of colloid suspension cannot be too high, while the size of particulate cannot be too large. Even for the new Zeta potentiometer (model Zetaprobe) by Colloidal Dynamics Inc., USA, the highest particulate density is only 60% (volume density). Thus, it is impossible to obtain a system with higher density, or "original state" measurement of solid particulate material.

Currently, Li Hang, et al. proposes a new method, i.e., with ion exchange equilibrium experiment and electrode method to realize combined measurement of five parameters including surface potential, specific surface area, surface charge density, total amount of surface charge and surface electric field intensity. This method marks a breakthrough in the field of determining surface property parameters of a substance. However, this method also has some weakness: (1) This method may need quite long time to determine the surface property, due to the method is based on ion exchange equilibrium experiment, and the ion exchange equilibrium in actual system often requires considerable time. (2) Due to different materials have different surface charge amount and charge density, the time required for ion exchange equilibrium may vary significantly. Thus, in practice, it may be difficult to control the equilibrium state with this method. (3) In this method, it is required to calibrate three parameters, i.e., $\beta_A$, $\beta_B$ and m with standard sample, in which $\beta_A$, $\beta_B$ may be easy to be accurately calibrated, but accurate calibration of m may have difficulty. (4) This method may first need to use strong acid to treat the sample to make the tested sample to be $H^+$ saturated, and thus may bring certain change to the substance surface property. In addition, the electrostatic bond between $H^+$ ion and surface is far greater than that of ions such as $Ca^{2+}$ and $Na^+$, which may cause difficulty to reach exchange equilibrium.

Thus, there is a need for a system and method for determining and analyzing surface property parameters of a substance, which can overcome the shortcomings such as long equilibrium time, not easy to determine equilibrium and not easy to accurately determine m.

SUMMARY

In view of above, the present invention provides a system and a method for determining and analyzing surface property parameters of a substance, which can overcome the shortcomings such as long equilibrium time, not easy to determine equilibrium and not easy to accurately determine the value of m. With kinetic measurement of ion exchange, the kinetic data obtained within short time is used to accurately predict equilibrium state, to overcome the difficulty of long equilibrium time and not easy to determine equilibrium, to directly determine the total amount of surface charge. Thus, in determining the specific surface area, the parameter of m would not be needed. This can overcome the difficulty in determining m. In addition, there is no need to make the sample to be $H^+$ saturated, to overcome the relevant issues brought by $H^+$ saturation.

One objective of the present invention is to provide a system for determining and analyzing surface property parameters of a substance based on a kinetic method. A further objective of the present invention is to provide a method for determining and analyzing surface property parameters of a substance based on a kinetic method.

One objective of the present invention can be achieved with the following technical solutions:

A system for determining and analyzing surface property parameters of a substance based on a kinetic method, comprising: a sample processing system and a detection system. The sample processing system includes a reactor, a collector for liquid to be tested, and a container for liquid to be tested. The reactor is used to receive substance to be tested and reacting liquid. The reactor and the collector for liquid to be tested are connected via a tube. The collector for liquid to be tested and the container for liquid to be tested are connected via a tube. The reacting liquid in the reactor flows into the collector for liquid to be tested. The liquid in the collector for liquid to be tested flows into the container for liquid to be tested.

The detection system includes a detecting electrode, a concentration and activity operator, a kinetic data processor, a surface property operation module, and a result output module. The detecting electrode is used to detect ion activity of solution in a sample containing unit. The concentration and activity operator is used to calculate concentration of the solution based on the ion activity obtained from the detecting electrode. The kinetic data processor is used to process and store data obtained from detecting and establish a linear regression equation, so as to obtain intercept and gradient of the line. The surface property operation module is used to calculate a surface property parameter of the substance based on the detected data. The result output module is used to output the surface property parameter of the substance. The detecting electrode, the concentration and activity operator, the kinetic data processor, the surface property operation module and the result output module are connected in order.

Yet, the surface property operation module includes a surface charge total amount operator, a surface potential operator, a surface charge density operator, a surface electric field intensity operator, and a specific surface area operator. The kinetic data processor is connected with the surface charge total amount operator and the surface potential operator. The surface potential operator is connected with the surface charge density operator. The surface charge density operator is connected with the surface electric field intensity operator. The surface charge density operator and the surface charge total amount operator are connected with the specific surface area operator. The result output module is connected with the surface charge total amount operator, the surface potential operator, the surface charge density operator, the surface electric field intensity operator, and the specific surface area operator, respectively.

Yet, the kinetic data processor establishes the linear regression equation through the following steps, to obtain the intercept and gradient of the line:

S1: y-coordinate: $y=[N_{\bar{B}}(t_{i+1})-N_{\bar{B}}(t_i)]/(t_{i+1}-t_i)$,
x-coordinate: $x=N_{\bar{B}}(t_i)+0.5[N_{\bar{B}}(t_{i+1})-N_{\bar{B}}(t_i)]$;

S2: drawing a linear image based on positions of the x-coordinate and y-coordinate in a rectangular coordinate system;

S3: obtaining the intercept p and gradient q of the line;

wherein, $N_{\bar{B}}(t_i)$ indicates accumulated adsorption amount of ion $B^{m+}$, $N_{\bar{B}}(t_i)$ is the accumulated adsorption amount of the sample to ion $B^{m+}$, upon reaction for $t=t_i$ minutes, in which $t_0$ is a pre-set interval, and $t_i$ is reaction time.

Yet, the system includes: a millivoltmeter, a constant flow pump, a liquid container, a constant temperature chamber and a thermostat (controller for constant temperature). The input of the millivoltmeter is connected with the detecting electrode, and the output of the millivoltmeter is connected with the concentration and activity operator. The constant flow pump is positioned between the reactor and the collector for liquid to be tested, for controlling the liquid flow velocity from the reactor to the collector for liquid to be tested. The system further includes: a first control valve, a second control valve, a third control valve, an automatic controller for valve, and a negative pressure suction pump. The first control valve is positioned between the collector for liquid to be tested and the container for liquid to be tested. The container for liquid to be tested is provided with the second control valve, which is connected with the negative pressure pump. The container for liquid to be tested is further provided with the third control valve that is connected with the negative pressure pump. The third control valve and the negative pressure pump are further provided with a waste liquid discharge outlet, which is used for discharging solution in the container for liquid to be tested. The automatic controller for valve is connected with the first control valve, the second control valve and the third control valve, respectively. The thermostat is connected with the constant flow pump. The liquid container is connected with the reactor. The sample processing system is positioned within the constant temperature chamber.

Yet, the surface charge total amount operator calculates the surface charge total amount of the substance to be tested by the following equation:

$$SCN = -m\frac{p_0}{q_0},$$

Wherein, SCN is the total amount of surface charge, m is the valence of ion $B^{m+}$, $p_0$ is the intercept of the line, and $q_0$ is the gradient of the line.

The surface potential operator calculates the potential on the surface of the substance to be tested by the following equation:

$$\varphi_0 = -\frac{RT}{(m\beta_B - n\beta_A)F} \ln\left[\frac{a_A^0}{a_B^0}\frac{p}{\left(q\frac{|SCN|}{n} + \frac{m}{n}p\right)}\right]^2,$$

Wherein, $\phi_0$ is the surface potential of the substance to be tested, $\beta_B$ and $\beta_A$ are effective charge coefficient of ion $B^{m+}$ and ion $A^{n+}$, respectively, F indicates Faraday constant, R indicates gas constant, T indicates temperature, m indicates valence of $B^{m+}$, n indicates valence of $A^{n+}$, p indicates intercept, q indicates gradient, $a_A^0$ and $a_B^0$ are respective activities of ion $A^{n+}$ and ion $B^{m+}$ in the bulk solution when reaction reaches equilibrium.

The surface charge density operator calculates the surface charge density of the substance to be tested by the following equation:

$$\sigma_0 \approx \text{sign}(\phi_0)\sqrt{\frac{\varepsilon RT}{2\pi F^2}\left[a_B^0\left(e^{-\frac{m\beta_B F\phi_0}{RT}} - 1\right) + a_A^0\left(e^{-\frac{n\beta_A F\phi_0}{RT}} - 1\right)\right]},$$

Wherein, $\sigma_0$ is the surface charge density, $\phi_0$ is the surface potential, and $\varepsilon$ is the dielectric constant of water.

The surface electric field intensity operator calculates the surface electric field intensity of the substance to be tested by the following equation:

$$E_0 = \frac{4\pi F}{\varepsilon}\sigma_0,$$

Wherein, $E_0$, is the surface electric field intensity of the substance to be tested.

The specific surface area operator calculates the specific surface area of the substance to be tested by the following equation:

$$S = \frac{SCN}{\sigma_0},$$

Wherein, S is the specific surface area of the substance to be tested.

Another objective of the present invention can be achieved by the following technical solutions:

A method for determining and analyzing surface property parameters of a substance based on a kinetic method, comprising the following steps:

S1: conducting $A^{n+}$ saturation to a surface of the substance to be tested with $AX_n$ electrolyte solution having known concentration;

wherein, the $AX_n$ electrolyte solution represents an electrolyte solution of metallic cation with charge amount of n, and ion $A^{n+}$ represents metallic cation with charge amount of n;

S2: having a solution of $BX_m$ electrolyte with known concentration to flow through the surface of the substance to be tested, to have ion $A^{n+}$ and ion $B^{m+}$ on the surface of the substance to be tested to perform fusion replacement;

wherein, solution of $BX_m$ electrolyte represents an electrolyte solution of metallic cation with charge amount of m, and ion $B^{m+}$ represents metallic cation with charge amount of m;

S3: collecting flow-out liquid that flows through the surface of the substance to be tested at pre-set interval;

S4: measuring activity of ion $B^{m+}$ in the flow-out liquid, and calculating concentration of ion $B^{m+}$;

S5: calculating accumulated adsorption amount of ion $B^+$ according to the following equation by using the concentration of ion $B^+$:

$$N_B(t_i) = \frac{1}{m}\sum_{i=1}^{t_i/t_0} V[f_{B0} - f_B(t_i)],$$

wherein, $N_B(t_i)$ is the accumulated adsorption amount of the sample to ion $B^{m+}$ upon reaction for $t=t_i$ minutes, m is sample mass, V is the volume of solution collected within the pre-set interval, $f_{B0}$ is the concentration of solution before ion $B^{m+}$ flows into the sample, $f_B(t_i)$ is the concentration of ion $B^{m+}$ in solution collected by ith time, $t_0$ is the pre-set interval, and $t_i$ is reaction time;

S6: using $N_B(t_i)$ (accumulated adsorption amount of ion $B^{m+}$), with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of the x-coordinate and y-coordinate in a rectangular coordinate system, and to obtain intercept of the line as $p_0$ and gradient of the line as $q_0$;

S7: calculating the surface charge total amount of the sample with intercept $p_0$ and gradient $q_0$ of the line according to the below equation:

$$SCN = -m\frac{p_0}{q_0},$$

wherein, SCN is the total amount of the surface charge, and m is valence of ion $B^{m+}$.

Yet, the step S4 comprises the following sub-steps to calculate concentration of ion $B^{m+}$ by using iterative algorithm:

S41: having the solution of $BX_m$ electrolyte with known concentration to flow through the surface of the substance to be tested, to have ion $A^{n+}$ and ion $B^{m+}$ on the surface of the substance to be tested to perform fusion replacement: $mSoil-A+nBX_m=nSoil-B+mAX_n$; obtaining a solution having $A^{n+}$, $B^{m+}$ and $X^-$, to calculate concentration of ion $A^{n+}$ and concentration of ion $B^{m+}$:

$$C_A = \left(\frac{m}{n}\right)C_B,$$

$C_X = mnC_B$;

wherein, $C_A$ represents concentration of ion $A^{n+}$, $C_B$ represents concentration of ion $B^{m+}$, $C_X$ represents concentration of ion $X^-$, Soil-A represents soil saturated with ion $A^{n+}$, and Soil-B represents soil saturated with ion $B^{m+}$;

S42: measuring activity of ion $B^{m+}$ in aqueous solution, with a measurement of ion $B^{m+}$ activity as $a_B$, using the ion activity as an initial concentration of ion $B^{m+}$ in the first iterative operation, i.e., $C_B^{(0)}=a_B$. Likewise, the initial concentration of ion $A^{n+}$ is:

$$C_A^{(0)} = \left(\frac{m}{n}\right)a_B.$$

S43: calculating concentration of ion $X^-$ in the first iterative operation to be $C_X^{(0)}=mna_B$, and ionic strength $I^{(1)}$ in the first iterative operation to be:

$$I^{(1)} = \frac{1}{2}\sum_i c_i^{(0)}Z_i^2 = \frac{1}{2}(m^2 a_B + mna_B + mna_B) = \frac{1}{2}(m^2+2mn)a_B,$$

wherein, $I^{(1)}$ represents ion strength coefficient in the first iterative operation, $Z_i$ represents valence of ion i, $c_i^{(0)}$ represents initial concentration of ion i in the iterative operation.

S44: obtaining initial activity coefficient of ion $B^{m+}$ in the system from Debye-Hückel limiting formula:

$$\gamma_B^{(1)} = \exp\left(-\frac{6030.2 \times T^{-\frac{3}{2}}|Z_+^2|\sqrt{I^{(1)}}}{1+\sqrt{I^{(1)}}}\right);$$

wherein, $\gamma_B^{(1)}$ represents initial activity coefficient of ion $B^{m+}$, $Z_+$ represents charge amount of positive ion, $I^{(1)}$ represents ion strength of the first iterative operation, and T represents temperature;

S45: calculating concentration $c_B^{(1)}$ of ion $B^{m+}$ after the first iteration:

$$c_B^{(1)} = \frac{a_B}{\gamma_B^{(1)}};$$

S46: calculating concentration $C_X^{(1)}$ of ion X after the first iteration:

$C_X^{(1)} = mnc_B^{(1)}$;

S47: respectively calculating ion strength and activity coefficients of the second iteration as:

$$I^{(2)} = \frac{1}{2}\sum_i c_i^{(1)}Z_i^2 = \frac{1}{2}(m^2+2mn)c_B^{(1)};$$

$$\gamma_B^{(2)} = \exp\left(-\frac{6030.2 \times T^{-\frac{3}{2}}|Z_+^2|\sqrt{I^{(2)}}}{1+\sqrt{I^{(2)}}}\right);$$

wherein, $\gamma_B^{(2)}$ represents ion activity coefficient of the second iteration, $c_B^{(1)}$ represents concentration of ion $B^{m+}$ after the first iteration, $Z_i$ represents valence of ion i, and $I^{(2)}$ represents ion strength of the second iteration;

S48: calculating concentration $c_B^{(2)}$ of ion $B^{m+}$ after the second iteration:

$$c_B^{(2)} = \frac{a_B}{\gamma_B^{(2)}};$$

S49: concentration of ion X after the second iterative operation shall be:

$C_X^{(2)} = mnc_B^{(2)}$;

S410: repeatedly iterating n times of the above steps S41-S49, and calculating according to the following equation:

$$I^{(n)} = \frac{1}{2}\sum_i c_i^{(n-1)}Z_i^2 = \frac{1}{2}(m^2+2mn)c_B^{(n-1)};$$

$$\gamma_B^{(n)} = \exp\left(-\frac{6030.2 \times T^{-\frac{3}{2}}|Z_+^2|\sqrt{I^{(n)}}}{1+\sqrt{I^{(n)}}}\right);$$

when satisfying $(I^{(n)}-I^{(n-1)})/I^{(n)}<0.001$, iteration is stopped, and the resulting concentration $c_B^{(n)}$ is:

$$c_B^{(n)} = \frac{a_B}{\gamma_B^{(n)}};$$

wherein, $I^{(n)}$ represents ion strength of nth iteration, $I^{(n-1)}$ represents ion strength of (n-1)th iteration, $c_B^{(n)}$ represents concentration of ion $B^{m+}$ after nth iteration, and $\gamma_B^{(n)}$ represents ion activity coefficient of nth iteration.

Yet, the below steps may be included following step S7:

S8: calculating ion strength I of the flow solution of mixed electrolyte having ion $A^{n+}$ and ion $B^{m+}$ according to the following equation:

$I=\frac{1}{2}[(n+n^2)f_{A0}+(m+m^2)f_{B0}]$ wherein, $f_{A0}$ is the solution concentration before ion $A^{n+}$ flows into the surface of the substance to be tested, and $f_{B0}$ is the solution concentration before ion $B^+$ flows into the surface of the substance to be tested;

S9: Substituting the ion strength of the flow liquid in Davies equation, to calculate ion $A^{n+}$ activity coefficient $\gamma_{A0}$ and ion $B^{m+}$ activity coefficient $\gamma_{B0}$;

S10: calculating activity of ion $A^{n+}$ and ion $B^{m+}$ according to the following equation:

$$a_A^0 = f_{A0}\gamma_{A0}\ a_B^0 = f_{B0}\gamma_{B0}$$

wherein, $\gamma_{A0}$ and $\gamma_{B0}$ are respective activity coefficient of ion $A^{n+}$ and ion $B^{m+}$ in bulk solution when reaction reaches equilibrium; $a_A^0$ and $a_B^0$ are respective activity of ion $A^{n+}$ and ion $B^{m+}$ in bulk solution when reaction reaches equilibrium.

The method may include the following steps after step S10:

S11: under a given pH condition, having a mixed electrolyte solution by $AX_n$ electrolyte solution with known concentration $f_{A0}$ and $BX_m$ electrolyte solution with known concentration $f_{B0}$ to flow through the surface of the substance to be tested, to have ion $A^{n+}$ and ion $B^{m+}$ on the surface of the substance to be tested to perform fusion replacement, and collecting the flow-out solution that flows through the surface of the substance to be tested in pre-set interval.

S12: repeating the steps of S1 to S6;

S13: using $N_B(t_i)$ (accumulated adsorption amount of ion $B^{m+}$), with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of x-coordinate and y-coordinate in a rectangular coordinate system, and to obtain intercept p and gradient q of the line.

The method further comprises the following steps after step S13:

S14: using the total charge amount obtained from step S7, the activity obtained from step S10, and the intercept p and gradient q of the line obtained from step S13, to substitute into the below equation to calculate the electric potential on the surface of the substance to be tested:

$$\varphi_0 = -\frac{RT}{(m\beta_B - n\beta_A)F}\ln\left[\frac{a_A^0}{a_B^0}\frac{p}{\left(q\frac{|SCN|}{n} + \frac{m}{n}p\right)}\right]^2,$$

wherein, $\varphi_0$ is the surface potential of the substance to be tested, $\beta_B$ and $\beta_A$ are effective charge coefficients of ion $B^{m+}$ and ion $A^{n+}$, F represents Faraday constant, R represents gas constant, and T represents temperature;

S15: substituting the electric potential on the surface of the substance to be tested in the following equation to calculate the surface charge density of the substance to be tested:

$$\sigma_0 \approx \text{sign}(\varphi_0)\sqrt{\frac{\varepsilon RT}{2\pi F^2}\left[a_B^0\left(e^{-\frac{m\beta_B F\varphi_0}{RT}} - 1\right) + a_A^0\left(e^{-\frac{n\beta_A F\varphi_0}{RT}} - 1\right)\right]},$$

wherein, $\sigma_0$ is the surface charge density (mol/dm$^2$), $\in$ is the dielectric constant of medium, in which water has $\in = 8.9 \times 10^{-10}$ C$^2$/(J·dm);

S16: substituting the surface charge density of the substance to be tested in the following equation to calculate the surface electric field intensity of the substance to be tested:

$$E_0 = \frac{4\pi F}{\varepsilon}\sigma_0,$$

wherein, $E_0$ represents the surface electric field intensity of the substance to be tested;

S17: substituting the total charge amount and the surface charge density of the substance to be tested in the following equation to calculate the specific surface area of the sample:

$$S = \frac{SCN}{\sigma_0},$$

wherein, S represents the specific surface area of the substance to be tested;

S18: outputting the measurement of the surface parameters of the substance to be tested, the output measurement of surface parameters of the substance to be tested includes: measurements of the surface potential of the substance to be tested, the surface charge total amount of the substance to be tested, the surface charge density of the substance to be tested, the surface electric field intensity of the substance to be tested, and the specific surface area of the substance to be tested.

Advantages of the present invention include: the present invention adopts an ion exchange kinetic method to overcome the difficulties such as long reaction equilibrium time, not easy to determine equilibrium and not easy to accurately determine the value of m, when measuring/determining surface property parameters of a substance. With kinetic data obtained in short time to accurately calculate, the above shortcomings can be overcome. Five parameters of the substance surface property can be calculated with only intercept and gradient of the linear regression equation obtained from the kinetic data. Further, with kinetic method, the total amount of surface charge can be directly determined, and thus the parameter of m no longer is needed in determining the specific surface area, which solves the issue occurred in determining m. In addition, this method does not need the sample to be H$^+$ saturated, which solves the relevant issues brought by H$^+$ saturation, thereby solving the issues associated with change in substance surface property brought by treating the sample with strong acid and hard to reach ion exchange equilibrium in the Fr saturated sample. Further, when the activity of ion $B^{m+}$ in the equilibrium liquid is much greater than that of H$^+$ in the solution, the electrostatic adsorption of H$^+$ can be negligible. This ensures that the present invention can be a common method suitable for any pH and any substance type.

Other advantages, objectives and features will be described in the following specification, and to some extent, which will be obvious to people skilled in the art based on studies, or which can be taught by implementing the present invention. The objectives and other advantages of the present invention can be achieved and obtained from the description, claims and drawings.

BRIEF DESCRIPTION OF DRAWINGS

To make the objectives, technical solutions and advantages of the present invention more clear, detailed description will be made to the present invention in combination with drawings, wherein.

Figure 1:
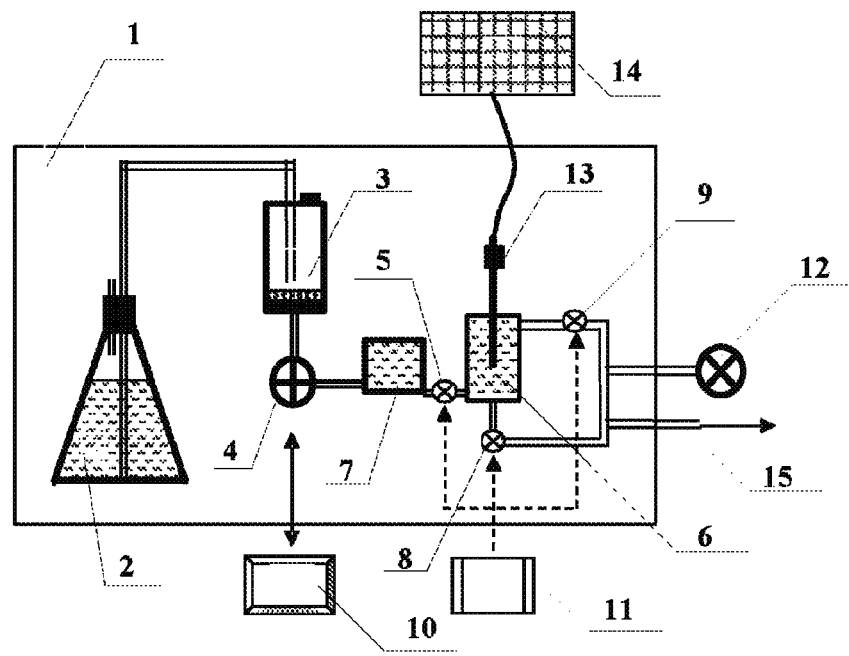
FIG. 1 is structural diagram showing a system for analyzing surface property parameters of a substance based on kinetic method, according to an embodiment of the present invention.

In the drawings, 1—constant temperature chamber, 2—liquid container, 3—reactor, 4—constant flow pump, 5—collector for liquid to be tested, 6—container for liquid to be tested, 7—first control valve, 8—second control valve, 9—third control valve, 10—thermostat (controller for constant temperature), 11—automatic controller for valve, 12—negative pressure pump, 13—detecting electrode, 14—detection system, 15—waste liquid discharge outlet.

DETAILED DESCRIPTION

Preferred embodiments will be described in detail in combination with the accompanying drawings. It shall be understood that the preferred embodiments are for illustrative only, and not for limiting the protection scope of the present invention.

FIG. 1 is structural diagram showing a system for analyzing surface property parameters of a substance based on kinetic method in accordance with an embodiment of the present invention. As shown in the drawing, a system for analyzing surface property parameters of a substance based on kinetic method is provided. The system comprises a sample processing system and a detection system. The sample processing system includes a reactor 3, a collector 5 for liquid to be tested, a container 6 for liquid to be tested, a millivoltmeter, a constant flow pump 4, a liquid container 2, a constant temperature chamber 1 and a thermostat (constant temperature controller) 10. The reactor 3 is used for containing the substance to be tested and the reaction liquid. The reactor 3 is connected with the collector 5 for liquid to be tested via a conduit. The collector 5 for liquid to be tested is connected with the container 6 for liquid to be tested via a conduit. The reaction liquid in the reactor 3 flows into the collector 5 for liquid to be tested. The liquid in the collector 5 for liquid to be tested flows into the container 6 for liquid to be tested. The input port of the millivoltmeter is connected with the detecting electrode 13, and the output port of the millivoltmeter is connected with the concentration and activity operator. The constant flow pump 4 is positioned between the reactor 3 and the collector 5 for liquid to be tested, for controlling liquid flow velocity from the reactor 3 to the collector 5 for liquid to be tested. The system further includes a first control valve 7, a second control valve 8, a third control valve 9, an automatic controller 11 for valve, and a negative pressure pump 12. The first control valve 7 is positioned between the collector 5 for liquid to be tested and the container 6 for liquid to be tested. The container 6 for liquid to be tested is provided with the second control valve 8 which is connected with the negative pressure pump 12. The container 6 for liquid to be tested is further provided with the third control valve 9 that is connected with the negative pressure pump 12. The third control valve 9 and the negative pressure pump 12 are provided with a waste liquid discharge outlet 15 that is used for draining solution in the container 6 for liquid to be tested. The automatic controller 11 for valve is connected with the first control valve 7, the second control valve 8 and the third control valve 9, respectively. The thermostat (controller) 10 is connected with the constant flow pump 4. The liquid container 2 is connected with the reactor 3. The sample processing system is disposed within the constant temperature chamber 1.

Figure 2:
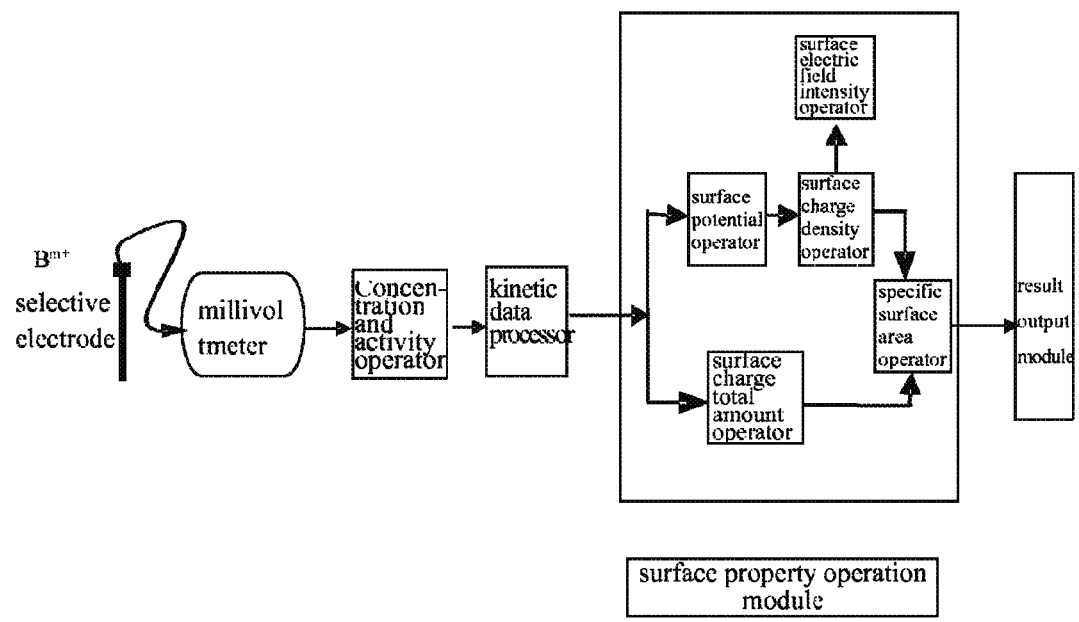
FIG. 2 is structural diagram showing a detection system in the system for analyzing surface property parameters of a substance based on kinetic method, according to an embodiment of the present invention.

FIG. 2 is structural diagram showing a detection system in the system for analyzing surface property parameters of a substance based on kinetic method in accordance with one embodiment of the present invention. As shown in FIG. 2, a detection system 14 for is provided. The detection system 14 comprises a detecting electrode 13, a concentration and activity operator, a kinetic data processor, a surface property operation module, and a result output module. The detecting electrode is used to detect ion activity of the solution in the sample containing unit. The concentration and activity operator is used to calculate concentration of the solution based on the ion activity obtained from the detecting electrode. The kinetic data processor is used to process and store the detected data and establish a linear regression equation, so as to obtain intercept and gradient of the line. The surface property operation module is used to calculate the substance surface property parameters based on the detected data. The result output module is used to output the substance surface property parameters. The detecting electrode, the concentration and activity operator, the kinetic data processor, the surface property operation module, and the result output module are connected in order.

The surface property operation module comprises a surface charge total amount operator, a surface potential operator, a surface charge density operator, a surface electric field intensity operator, and a specific surface area operator. The kinetic data processor is connected with the surface charge total amount operator and the surface potential operator. The surface potential operator is connected with the surface charge density operator. The surface charge density operator is connected with the surface electric field intensity operator. The surface charge density operator and the surface charge total amount operator are connected with the specific surface area operator. The result output module is connected with the surface charge total amount operator, the surface potential operator, the surface charge density operator, the surface electric field intensity operator, and the specific surface area operator, respectively.

Figure 3:
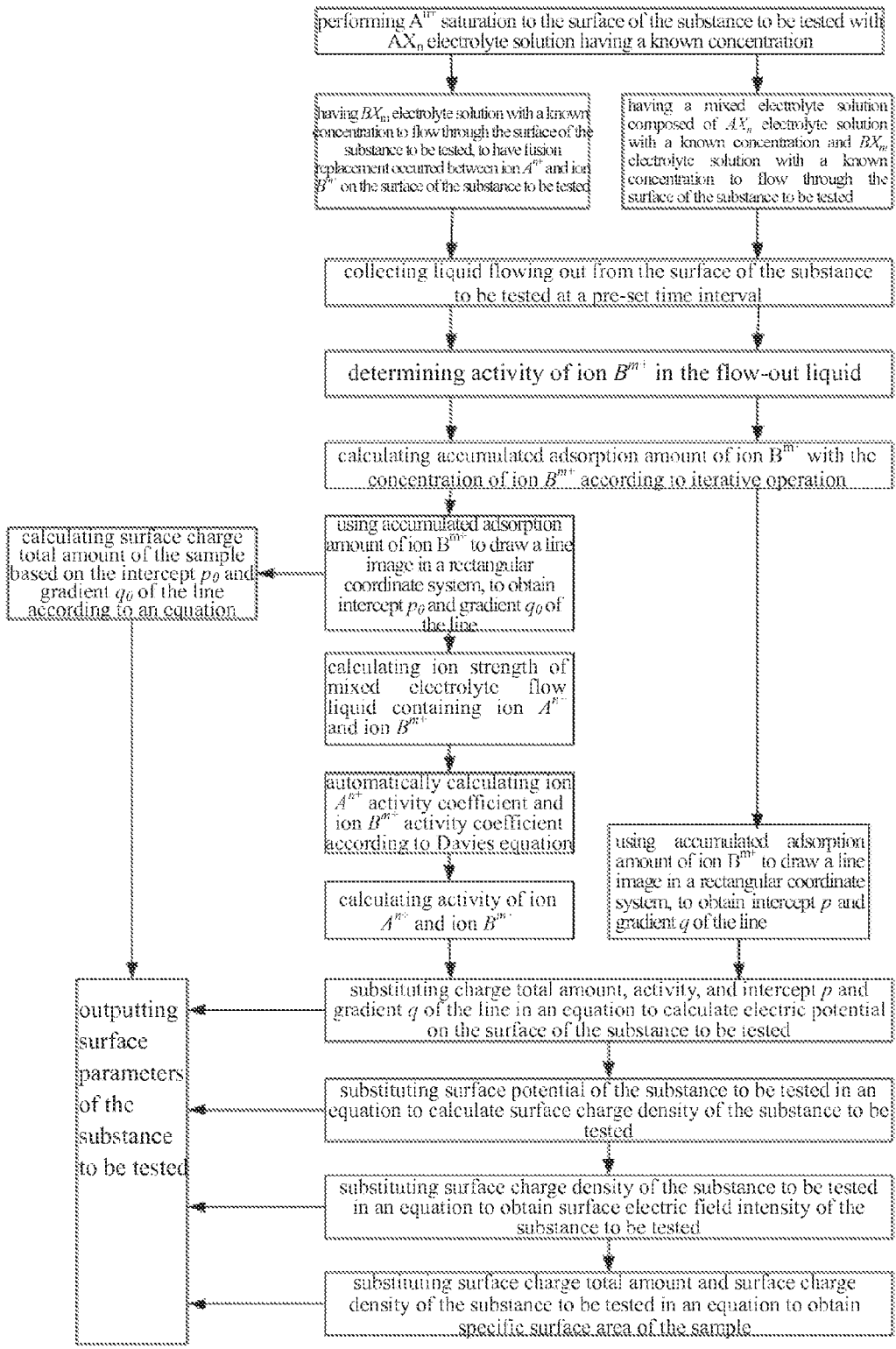
FIG. 3 is flow chart of a system for analyzing surface property parameters of a substance based on kinetic method, according to an embodiment of the present invention.

FIG. 3 is a flow chart of a system for analyzing surface property parameters of a substance based on kinetic method in accordance with one embodiment of the present invention. As shown in FIG. 3, a kinetic method for determining surface property parameters of a substance is provided. The analyzing system operates as follows.

$A^{n+}$ saturation is performed to the substance to be tested with $AX_n$ electrolyte solution having known concentration. The $A^{n+}$ saturated substance to be tested then is disposed in the reactor. The constant flow pump is set to control the flowing liquid to flow at a desired velocity (e.g., 1 ml/min). Under a given pH condition, the electrolyte solution of another positive ion $B^{m+}$ having known concentration of charge amount m evenly flows through the sample in the reactor at a pre-set flow velocity, where fusion replacement occurs between $A^{n+}$ and $B^{m+}$. When the first drop of liquid flows out the reactor outlet, the automatic controller for valve starts the clock (at this moment, the first control valve 7, the second control valve 8 and the third control valve 9 are in automatic close state). Based on the set interval (e.g., 5 minute), the first control valve 7, the third control valve 9 and the negative pressure pump simultaneously open/turn on, to transfer the collected liquid from the collector for liquid to be tested to the container for liquid to be tested. Then, the first control valve 7 and the third control valve 9 are closed. The activity of $B^{m+}$ in the container for liquid to be tested is measured with a detector. Then, concentration of $B^{m+}$ is calculated with the concentration and activity operator in the detector by using iterative operation. The obtained concentration is stored in the "kinetic data processor" in the detector. Then, the second control valve 8 and the negative pressure pump will open/turn on, to drain the solution in the liquid container. The system automatically repeat collection of liquid from the reactor outlet, so as to obtain and store concentration of $B^{m+}$ in the collected liquid at each time interval (e.g., 5 minute). With concentration of $B^{m+}$ in the collected liquid obtained at each time interval, accumulated adsorption amounts of $B^{m+}$ at different time are calculated and stored in the kinetic data processor in the detector. By using the data of accumulated adsorption amounts obtained, data is automatically processed and stored in the kinetic data processor. All the operation results of individual operators in the detector are output, including the values of the surface potential of the substance to be tested, the surface charge total amount of the substance to be tested, the surface charge density of the substance to be tested, the surface electric field intensity of the substance to be tested, and the specific surface area of the substance to be tested.

A kinetic method for determining surface property parameters of a substance is provided, comprising the steps of:

S1: performing $A^{n+}$ saturation to a surface of the substance to be tested with $AX_n$ electrolyte solution having known concentration;

wherein, $AX_n$ electrolyte solution represents an electrolyte solution of metallic cation with a charge amount of n, and ion $A^{n+}$ represents metallic cation with a charge amount of n;

S2: having $BX_m$ electrolyte solution with known concentration to flow through the surface of the substance to be tested, to have fusion replacement occurred between $A^{n+}$ and $B^{m+}$ on the surface of the substance to be tested;

wherein, $BX_m$ electrolyte solution represents an electrolyte solution of metallic cation with a charge amount of m, and ion $B^{m+}$ represents metallic cation with a charge amount of m;

S3: collecting liquid flowing out from the surface of the substance to be tested at a pre-set time interval;

S4: determining activity of ion $B^{m+}$ in the flow-out liquid, and calculating concentration of ion $B^{m+}$ by using iterative operation;

S5: calculating accumulated adsorption amount of ion $B^{m+}$ with the concentration of ion $B^{m+}$ according to the following iterative equation:

$$N_B(t_i) = \frac{1}{m} \sum_{i=1}^{t_i/t_0} V[f_{B0} - f_B(t_i)] \qquad (1)$$

wherein, $N_B(t_i)$ is the accumulated adsorption amount of ion $B^{m+}$ by the sample upon reaction for $t=t_i$ minutes, with unit as mol/g; m is sample mass, with unit as g; V is the volume of solution collected within pre-set interval, with unit as liter, i.e., l; $f_{B0}$ is the solution concentration before ion $B^{m+}$ flows into the sample, with unit as mol/l; $f_B(t_i)$ is concentration of ion $B^{m+}$ in the solution collected at ith time, with unit as mol/l; $t_0$ is pre-set time interval, and $t_i$ is reaction time, with unit as min;

S6: using the accumulated adsorption amount $N_B(t_i)$ of ion $B^{m+}$, with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of x-coordinate and y-coordinate in a rectangular coordinate system, to obtain intercept $p_0$ and gradient $q_0$ of the line;

S7: calculating the surface charge total amount of the sample based on the intercept $p_0$ and gradient $q_0$ of the line according to the following equation:

$$SCN = -m\frac{p_0}{q_0} \qquad (2)$$

wherein, SCN is the total amount of surface charge, with a unit as mol/g; and, m is valence of ion $B^+$.

S8: calculating ion strength of the mixed electrolyte flow liquid having ion $A^{n+}$ and ion $B^{m+}$ according to the following equation:

$$I=\tfrac{1}{2}[(n+n^2)f_{A0}+(m+m^2)f_{B0}] \qquad (3)$$

wherein, $f_{A0}$ is the solution concentration before ion $A^{n+}$ flows into the surface of the substance to be tested, and, $f_{B0}$ is the solution concentration before ion $B^{m+}$ flows into the surface of the substance to be tested;

S9: Substituting the ion strength of the flow liquid in Davies equation, to calculate ion $A^{n+}$ activity coefficient $\gamma_{A0}$ and ion $B^{m+}$ activity coefficient $\gamma_{B0}$;

S10: calculating activity of ion $A^{n+}$ and ion $B^{m+}$ according to the following equation:

$$a_A^0 = f_0\gamma_{A0} \quad a_B^0 = f_{B0}\gamma_{B0} \qquad (4)$$

wherein, $\gamma_{A0}$ and $\gamma_{B0}$ are respective activity coefficient of ion $A^{n+}$ and ion $B^{m+}$ in bulk solution when reaction reaches equilibrium; and, $a_A^0$ and $a_B^0$ are respective activity of ion $A^{n+}$ and ion $B^{m+}$ in bulk solution when reaction reaches equilibrium.

S11: under a given pH condition, having a mixed electrolyte solution of $AX_n$ electrolyte solution with a known concentration $f_{A0}$ and $BX_m$ electrolyte solution with a known concentration $f_{B0}$ to flow through the surface of the substance to be tested, to have fusion replacement occurred between ion $A^{n+}$ and ion $B^{m+}$ on the surface of the substance to be tested, and, collecting liquid flowing out from the surface of the substance to be tested at the pre-set time interval.

S12: repeating the steps of S1-S6;

S13: using the accumulated adsorption amount $N_B(t_i)$ of ion $B^+$, with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of x-coordinate and y-coordinate in a rectangular coordinate system, to obtain intercept p and gradient q of the line.

S14: substituting the charge total amount obtained from step S7, the activity obtained from step S10, and the intercept p and gradient q of the line obtained from step S13 in the following equation, to calculate electric potential on the surface of the substance to be tested:

$$\varphi_0 = -\frac{RT}{(m\beta_B - n\beta_A)F}\ln\left[\frac{a_A^0}{a_B^0}\left(q\frac{|SCN|}{n} + \frac{m}{n}p\right)\right]^2 \qquad (5)$$

wherein, $\phi_0$ is the surface electric potential of the substance to be tested, $\beta_B$ and $\beta_A$ are effective charge coefficients of ion $B^{m+}$ and ion $A^{n+}$, F represents Faraday constant, R represents gas constant, and T represents temperature.

S15: substituting the surface electric potential of the substance to be tested in the following equation to calculate surface charge density of the substance to be tested:

$$\sigma_0 \approx \text{sign}(\phi_0)\sqrt{\frac{\varepsilon RT}{2\pi F^2}\left[a_B^0\left(e^{-\frac{m\beta_B F\phi_0}{RT}}-1\right)+a_A^0\left(e^{-\frac{n\beta_A F\phi_0}{RT}}-1\right)\right]} \quad (6)$$

wherein, $\sigma_0$ is surface charge density (mol/dm$^2$), s is medium dielectric constant, in which water has $\varepsilon=8.9\times10^{-10}$ C$^2$/J·dm.

S16: substituting the surface charge density of the substance to be tested in the following equation to calculate surface electric field intensity of the substance to be tested:

$$E_0 = \frac{4\pi F}{\varepsilon}\sigma_0 \quad (7)$$

wherein, $E_0$ represents the surface electric field intensity (V/dm) of the substance to be tested;

S17: substituting the surface charge total amount and the surface charge density of the substance to be tested in the following equation, to obtain specific surface area of the sample:

$$S = \frac{SCN}{\sigma_0} \quad (8)$$

wherein, S represents specific surface area (dm$^2$/g) of the substance to be tested.

S18: outputting the value of the surface potential of the substance to be tested, the surface charge total amount of the substance to be tested, the surface charge density of the substance to be tested, the surface electric field intensity of the substance to be tested, and the specific surface area of the substance to be tested.

The above embodiments are only the preferred embodiments of the present invention, and shall not be used to limit the present invention. Apparently, people skilled in the art can modify the present invention, without departing from the spirit and scope of the present invention. As such, if such modifications fall in the scope of the appended claims and/or equivalent thereto, they are intended to be included in the present invention.

The invention claimed is:

1. A system for determining and analyzing surface property parameters of a substance based on kinetic method, comprising a sample processing system and a detection system;

the sample processing system including a reactor, a collector for liquid to be tested and a container for liquid to be tested; the reactor is used for containing the substance to be tested and reaction liquid; the reactor is connected with the collector for liquid to be tested via a conduit; the collector for liquid to be tested is connected with the container for liquid to be tested via a conduit; the reaction liquid in the reactor flows into the collector for liquid to be tested; the liquid in the collector for liquid to be tested flows into the container for liquid to be tested;

the detection system including a detecting electrode, a concentration and activity operator, a kinetic data processor, a surface property operation module, and a result output module; the detecting electrode is used for detecting an ion activity of solution in a sample container; the concentration and activity operator is used for calculating concentration of the solution based on the ion activity obtained from the detecting electrode; the kinetic data processor is used for processing and storing data obtained from detecting and establishes a linear regression equation to obtain intercept and gradient of a line; the surface property operation module is used for calculating the surface property parameters of the substance based on detected data; the result output module is used for outputting the surface property parameters of the substance; the detecting electrode, the operator concentration and activity, the kinetic data processor, the surface property operation module, and the result output module are connected in order.

2. The system for determining and analyzing surface property parameters of a substance based on kinetic method according to claim 1, wherein: the surface property operation module comprises a surface charge total amount operator, a surface potential operator, a surface charge density operator, a surface electric field intensity operator, and a specific surface area operator; the kinetic data processor is connected with the surface charge total amount operator and the surface potential operator; the surface potential operator is connected with the surface charge density operator; the surface charge density operator is connected with the surface electric field intensity operator; the surface charge density operator and the surface charge total amount operator are connected with the specific surface area operator; the result output module is respectively connected with the surface charge total amount operator, the surface potential operator, the surface charge density operator, the surface electric field intensity operator, and the specific surface area operator.

3. The system for determining and analyzing surface property parameters of a substance based on kinetic method according to claim 1, wherein: the kinetic data processor establishes the linear regression equation through the following steps, to obtain the intercept and gradient of the line:

S1: y-coordinate is y=[$N_B(t_{i+1})-N_B(t_i)$]/($t_{i+1}-t_i$), x-coordinate is x=$N_B(t_i)$+0.5[$N_B(t_{i+1})-N_B(t_i)$];

S2: drawing a line image based on x-coordinate and y-coordinate in a rectangular coordinate system;

S3: obtaining the intercept p and gradient q of the line; wherein, $N_B(t_i)$ represents an accumulated adsorption amount of ion B$^{m+}$, $N_B(t_i)$ is the accumulated adsorption amount of the sample to ion B$^{m+}$ upon reaction for t=$t_i$ minutes, $t_0$ is a pre-set time interval, and $t_i$ is a reaction time.

4. The system for determining and analyzing surface property parameters of a substance based on kinetic method according to claim 3, further comprising: a millivoltmeter, a constant flow pump, a liquid container, a constant temperature chamber and a thermostat; an input port of the millivoltmeter is connected with the detecting electrode; an output port of the millivoltmeter is connected with the concentration and activity operator; the constant flow pump is positioned between the reactor and the collector for liquid to be tested, for controlling liquid flow velocity from the reactor to the collector for liquid to be tested;

further comprising: a first control valve, a second control valve, a third control valve, an automatic controller for valve and a negative pressure pump; the first control valve is positioned between the collector for liquid to be tested and the container for liquid to be tested; the container for liquid to be tested is provided with the second control valve that is connected with the negative pressure pump; the container for liquid to be tested is further provided with the third control valve that is connected with the negative pressure pump; the third control valve and the negative pressure pump are provided with a waste liquid discharge outlet for draining liquid from the container for liquid to be tested; the automatic controller for valve is connected with the first control valve, the second control valve and the third control valve, respectively; the thermostat is connected with the constant flow pump; the liquid container is connected with the reactor; and, the sample processing system is positioned within the constant temperature chamber.

5. The system for determining and analyzing surface property parameters of a substance based on kinetic method according to claim 2, wherein: the surface charge total amount operator calculates the total amount of surface charge of the substance to be tested with the following equation:

$$SCN = -m\frac{p_0}{q_0},$$

wherein, SCN is the total amount of surface charge, m is valence of ion $B^{m+}$, $p_0$ is intercept of the line, and $q_0$ is gradient of the line.

6. The system for determining and analyzing surface property parameters of a substance based on kinetic method according to claim 2, wherein: the surface potential operator calculates the surface potential of the substance to be tested with the following equation:

$$\varphi_0 = -\frac{RT}{(m\beta_B - n\beta_A)F} \ln\left[\frac{a_A^0}{a_B^0} \frac{p}{\left(q\frac{|SCN|}{n} + \frac{m}{n}p\right)}\right]^2,$$

wherein, $\phi_0$ is the surface potential of the substance to be tested, $\beta_B$ and $\beta_A$ are effective charge coefficients of ion $B^{m+}$ and ion $A^{n+}$, F represents Faraday constant, R represents gas constant, T represents temperature, m represents valence of ion $B^{m+}$, n represents valence of ion $A^{n+}$, p represents intercept, q represents gradient, $a_A^0$ and $a_B^0$ are respective activity of ion $A^{n+}$ and ion $B^{m+}$ in bulk solution when reaction reaches equilibrium;

the surface charge density operator calculates the surface charge density of the substance to be tested with the following equation:

$$\sigma_0 \approx \text{sign}(\phi_0)\sqrt{\frac{\varepsilon RT}{2\pi F^2}\left[a_B^0\left(e^{-\frac{m\beta_B F\phi_0}{RT}} - 1\right) + a_A^0\left(e^{-\frac{n\beta_A F\phi_0}{RT}} - 1\right)\right]},$$

wherein, $\sigma_0$ is the surface charge density, $\phi_0$ represents the surface potential, and $\in$ is the medium dielectric constant of water;

the surface electric field intensity operator calculates the surface electric field intensity of the substance to be tested with the following equation:

$$E_0 = \frac{4\pi F}{\varepsilon}\sigma_0,$$

wherein, $E_0$ represents the surface electric field intensity of the substance to be tested;

the specific surface area operator calculates the specific surface area of the substance to be tested with the following equation:

$$S = \frac{SCN}{\sigma_0},$$

wherein, S represents the specific surface area of the substance to be tested.

7. A process according to the system for determining and analyzing surface property parameters of a substance based on kinetic method of claim 1, comprising the following steps:

S1: performing $A^{n+}$ saturation to the surface of the substance to be tested with $AX_n$ electrolyte solution having a known concentration;
wherein, the $AX_n$ electrolyte solution represents an electrolyte solution of metallic cation with a charge amount of n, and ion $A^{n+}$ represents a metallic cation with a charge amount of n;

S2: having a $BX_m$ electrolyte solution with a known concentration to flow through the surface of the substance to be tested, to have fusion replacement occurred between ion $A^{n+}$ and ion $B^{m+}$ on the surface of the substance to be tested;
wherein, $BX_m$ electrolyte solution represents an electrolyte solution of a metallic cation with a charge amount of m, and ion $B^{m+}$ represents a metallic cation with a charge amount of m;

S3: collecting liquid that flows out from the surface of the substance to be tested at the pre-set time interval;

S4: determining an activity of ion $B^{m+}$ in the flow-out liquid, and calculating an concentration of ion $B^{m+}$;

S5: using the concentration of ion $B^{m+}$ to calculate an accumulated adsorption amount of ion $B^{m+}$ according to the following equation:

$$N_B(t_i) = \frac{1}{m}\sum_{i=1}^{t_i/t_0} V[f_{B0} - f_B(t_i)],$$

wherein, $N_B(t_i)$ is the accumulated adsorption amount of the sample to ion $B^{m+}$ upon reaction for $t=t_i$ minutes, m is sample mass, V is an volume of liquid collected within the pre-set time interval, $f_{B0}$ is a solution concentration before ion $B^{m+}$ flows into the sample, $f_B(t_i)$ is concentration of ion $B^{m+}$ in liquid collected at ith time, $t_0$ is the pre-set time interval, and $t_i$ is reaction time;

S6: using the accumulated adsorption amount $N_B(t_i)$ of ion $B^{m+}$, with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of x-coordinate and y-coordinate in a rectangular coordinate system, to obtain intercept $p_0$ and gradient $q_0$ of the line;

S7: calculating the surface charge total amount of the sample based on intercept $p_0$ and gradient $q_0$ of the line according to the following equation:

$$SCN = -m\frac{p_0}{q_0},$$

wherein, SCN is the total amount of surface charge, and m is valence of ion $B^{m+}$.

8. The process of claim 7, wherein: step S4 further comprises the following steps:

S41: having $BX_m$ electrolyte solution with a known concentration to flow through the surface of the substance to be tested, to have fusion replacement occurred between ion $A^{n+}$ and ion $B^{m+}$ on the surface of the substance to be tested: $mSoil-A+nBX_m=nSoil-B+mAX_n$; obtaining a solution having $A^{n+}$, $B^{m+}$ and $X^-$, and calculating concentration of ion $A^{n+}$ and concentration of ion $B^{m+}$:

$$C_A = \left(\frac{m}{n}\right)C_B,$$

$C_X = mnC_B$;

wherein, $C_A$ represents concentration of ion $A^{n+}$, $C_B$ represents concentration of ion $B^{m+}$, $C_X$ represents concentration of $X^-$, Soil-A represents soil saturated by ion $A^{n+}$, and Soil-B represents soil saturated by ion $B^{m+}$;

S42: determining activity of ion $B^{m+}$ in aqueous solution, with a measurement of ion $B^{m+}$ activity as $a_B$; using the ion activity as an initial concentration of ion $B^{m+}$ for a first iterative operation $C_B^{(0)}=a_B$, and an initial concentration of ion $A^{n+}$ is:

$$C_A^{(0)} = \left(\frac{m}{n}\right)a_B;$$

S43: calculating concentration of ion X in the first iterative operation to be $C_X^{(0)}=mna_B$; and ion strength $I^{(1)}$ in the first iterative operation is:

$$I^{(1)} = \frac{1}{2}\sum_i c_i^{(0)}Z_i^2 = \frac{1}{2}(m^2 a_B + mna_B + mna_B) = \frac{1}{2}(m^2 + 2mn)a_B,$$

wherein, $I^{(1)}$ represents ion strength coefficient in the first iterative operation, $Z_i$ is valence of ion i, $c_i^{(0)}$ is the initial concentration of ion i in iterative operation;

S44: with Debye-Hückel limiting formula to obtain an initial activity coefficient of ion $B^{m+}$ as:

$$\gamma_B^{(1)} = \exp\left(-\frac{6030.2 \times T^{-\frac{3}{2}}|Z_+^2|\sqrt{I^{(1)}}}{1+\sqrt{I^{(1)}}}\right);$$

wherein, $\gamma_B^{(1)}$ represents initial activity coefficient of ion $B^{m+}$, $Z_+$ represents charge amount positive ion, $I^{(1)}$ represents ion strength of the first iterative operation, and T represents temperature;

S45: calculating concentration $c_B^{(1)}$ of ion $B^{m+}$ after the first iteration operation:

$$c_B^{(1)} = \frac{a_B}{\gamma_B^{(1)}};$$

S46: calculating concentration of ion X after the first iterated operation as $C_X^{(1)}$:

$C_X^{(1)} = mnc_B^{(1)}$;

S47: respectively calculating ion strength and activity coefficient of a second iteration as:

$$I^{(2)} = \frac{1}{2}\sum_i c_i^{(1)}Z_i^2 = \frac{1}{2}(m^2 + 2mn)c_B^{(1)};$$

$$\gamma_B^{(2)} = \exp\left(-\frac{6030.2 \times T^{-\frac{3}{2}}|Z_+^2|\sqrt{I^{(2)}}}{1+\sqrt{I^{(2)}}}\right);$$

wherein, $\gamma_B^{(2)}$ represents ion activity coefficient of the second iteration, $c_B^{(1)}$ represents concentration of ion $B^{m+}$ after the first iteration, represents valence of ion i, and $I^{(2)}$ represents ion strength of the second iteration;

S48: calculating concentration $c_B^{(2)}$ of ion $B^{m+}$ after the second iteration:

$$c_B^{(2)} = \frac{a_B}{\gamma_B^{(2)}};$$

S49: concentration of ion X after the second iteration is:

$C_X^{(2)} = mnc_B^{(2)}$;

S410: repeating iteration for n times according to the steps S41-S49, and calculating in accordance with the following equation:

$$I^{(n)} = \frac{1}{2}\sum_i c_i^{(n-1)}Z_i^2 = \frac{1}{2}(m^2 + 2mn)c_B^{(n-1)};$$

$$\gamma_B^{(n)} = \exp\left(-\frac{6030.2 \times T^{-\frac{3}{2}}|Z_+^2|\sqrt{I^{(n)}}}{1+\sqrt{I^{(n)}}}\right);$$

when satisfying $(I^{(n)}-I^{(n-1)})/I^{(n)}<0.001$, iteration is stopped, and a resulting concentration $c_B^{(n)}$ is:

$$c_B^{(n)} = \frac{a_B}{\gamma_B^{(n)}};$$

wherein, $I^{(n)}$ represents ion strength of nth iteration, $I^{(n-1)}$ represents ion strength of (n-1)th iteration, $c_B^{(n)}$ represents concentration of ion $B^{m+}$ after nth iteration, and $\gamma_B^{(n)}$ represents ion activity coefficient after nth iteration.

9. The process of claim 7, further comprising the below steps following step S7:

S8: calculating ion strength I of the mixed electrolyte flow liquid containing ion $A^{n+}$ and ion $B^{m+}$ according to the following equation:

$I=\frac{1}{2}[(n+n^2)f_{A0}+(m+m^2)f_{B0}]$ wherein, $f_{A0}$ is a solution concentration before ion $A^{n+}$ flows into the surface of the substance to be tested, and $f_{B0}$ is a solution concentration before ion $B^{m+}$ flows into the surface of the substance to be tested;

S9: substituting the ion strength of the flow liquid in Davies equation, to calculate ion $A^{n+}$ activity coefficient $\gamma_{A0}$ and ion $B^{m+}$ activity coefficient $\gamma_{B0}$;

S10: respectively calculating activity of ion $A^{n+}$ and ion $B^{m+}$ according to the following equation:

$$a_A^0 = f_{A0}\gamma_{A0} \quad a_B^0 = f_{B0}\gamma_{B0}$$

wherein, $\gamma_{A0}$ and $\gamma_{B0}$ are respective activity coefficient of ion $A^{n+}$ and ion $B^{m+}$ in bulk solution when reaction reaches equilibrium; and, $a_A^0$ and $a_B^0$ are respective activity of ion $A^{n+}$ and ion $B^{m+}$ in bulk solution when reaction reaches equilibrium.

10. The process of claim 9, further comprising the below steps following step S10:

S11: under a given pH condition, having a mixed electrolyte solution composed by $AX_n$ electrolyte solution with a known concentration $f_{A0}$ and $BX_m$ electrolyte solution with a known concentration $f_{B0}$ to flow through the surface of the substance to be tested, to have fusion replacement occurred between ion $A^{n+}$ and ion $B^{m+}$ on the surface of the substance to be tested, and collecting liquid that flows out from the surface of the substance to be tested at the pre-set time interval;

S12: repeating steps S1 to S6;

S13: using the accumulated adsorption amount $N_B(t_i)$ of ion $B^{m+}$, with y-coordinate as $y=[N_B(t_{i+1})-N_B(t_i)]/(t_{i+1}-t_i)$ and corresponding x-coordinate as $x=N_B(t_i)+0.5[N_B(t_{i+1})-N_B(t_i)]$, to draw a line image based on positions of x-coordinate and y-coordinate in a rectangular coordinate system, to obtain intercept p and gradient q of the line.

11. The process of claim 10, further comprising the below steps following step S13:

S14: substituting the charge total amount obtained from step S7, the activity obtained from step S10, and the intercept p and gradient q of the line obtained from step S13 in the following equation to calculate the surface potential of the substance to be tested:

$$\varphi_0 = -\frac{RT}{(m\beta_B - n\beta_A)F} \ln\left[\frac{a_A^0}{a_B^0} \frac{p}{\left(q\frac{|SCN|}{n} + \frac{m}{n}p\right)}\right]^2,$$

wherein, $\phi_0$ is the surface potential of the substance to be tested, $\beta_B$ and $\beta_A$ are effective charge coefficients of ion $B^{m+}$ and ion $A^{n+}$, F represents Faraday constant, R represents gas constant, and T represents temperature.

12. The process of claim 11, further comprising the below steps following step S14:

S15: substituting the surface potential of the substance to be tested in the following equation to calculate the surface charge density of the substance to be tested:

$$\sigma_0 \approx \text{sign}(\phi_0)\sqrt{\frac{\varepsilon RT}{2\pi F^2}\left[a_B^0\left(e^{-\frac{m\beta_B F\phi_0}{RT}} - 1\right) + a_A^0\left(e^{-\frac{n\beta_A F\phi_0}{RT}} - 1\right)\right]},$$

wherein, $\sigma_0$ is the surface charge density (mol/dm$^2$), and $\in$ is the medium dielectric constant, in which water has $\in = 8.9 \times 10^{-10}$ C$^2$/(J·dm).

13. The process of claim 12, further comprising the below steps following step S15:

S16: substituting the surface charge density of the substance to be tested in the following equation to calculate the surface electric field intensity of the substance to be tested:

$$E_0 = \frac{4\pi F}{\varepsilon}\sigma_0,$$

wherein, $E_0$ represents the surface electric field intensity of the substance to be tested.

14. The process of claim 13, further comprising the below steps following step S16:

S17: substituting the surface charge total amount and the surface charge density of the substance to be tested in the following equation to obtain the specific surface area of the sample:

$$S = \frac{SCN}{\sigma_0},$$

wherein, S represents the specific surface area of the substance to be tested.

15. The process of claim 14, further comprising the below steps following step S17:

S18: outputting surface parameters of the substance to be tested, the surface parameters includes: surface potential of the substance to be tested, surface charge total amount of the substance to be tested, surface charge density of the substance to be tested, surface electric field intensity of the substance to be tested, and specific surface area of the substance to be tested.

* * * * *